(12) United States Patent
Lee-Chen et al.

(10) Patent No.: US 10,064,838 B2
(45) Date of Patent: Sep. 4, 2018

(54) METHOD FOR TREATING TAU-ASSOCIATED DISEASES USING TETRAHYDROPYRANOL DERIVATIVES

(71) Applicant: NATIONAL TAIWAN NORMAL UNIVERSITY, Taipei (TW)

(72) Inventors: Guey-Jen Lee-Chen, Taipei (TW); Kwun-Min Chen, Taipei (TW)

(73) Assignee: National Taiwan Normal University, Taipei (TW)

( * ) Notice: Subject to any disclaimer, the term of this patent is extended or adjusted under 35 U.S.C. 154(b) by 0 days.

(21) Appl. No.: 15/434,601

(22) Filed: Feb. 16, 2017

(65) Prior Publication Data
US 2018/0042889 A1 Feb. 15, 2018

(30) Foreign Application Priority Data

Aug. 10, 2016 (TW) .............................. 105125369 A

(51) Int. Cl.
*A61K 31/351* (2006.01)
*A61K 31/381* (2006.01)
(52) U.S. Cl.
CPC .......... *A61K 31/351* (2013.01); *A61K 31/381* (2013.01)
(58) Field of Classification Search
CPC ............................ A61K 31/351; A61K 31/381
USPC ....................................................... 514/444
See application file for complete search history.

(56) References Cited

U.S. PATENT DOCUMENTS

| | | | |
|---|---|---|---|
| 3,655,695 A | 4/1972 | Andrews et al. | |
| 7,179,463 B2 * | 2/2007 | Lannfelt ............ | C07K 14/4711 424/130.1 |
| 9,629,835 B1 * | 4/2017 | Lee-Chen .......... | A61K 31/4709 |

FOREIGN PATENT DOCUMENTS

WO       WO 9403469 A1      2/1994

OTHER PUBLICATIONS

Chang et al, Drug design, Development and Therapy, 2016, 10, 885-896 (Year: 2016).*
Chang et al, CNS Neuroscience & Theraputics, 2017, 23, 45-56 (Year: 2017).*
Lin et al Europian Journal of Pharmaceutical Sciences, 2016, 89, 11-19 (Year: 2016).*
Ramani Gurubrahaman et al.; "Control of Five Contiguous Stereogenic Centers in an Organocatalytic Kinetic Resolution via Michael/Acetalization Sequence: Synthesis of Fully Substituted Tetrahydropyranols," Organic Letters, American Chemical Society; Jan. 8, 2015; 17; pp. 430-433.

* cited by examiner

*Primary Examiner* — Yevgeny Valenrod
(74) *Attorney, Agent, or Firm* — Muncy, Geissler, Olds & Lowe, P.C.

(57) ABSTRACT

A method for treating tau-associated disease by administering a pharmaceutical composition comprising a tetrahydropyranol derivative to a subject in need is disclosed. Particularly, a method for treating Alzheimer's disease by administering a pharmaceutical composition comprising a tetrahydropyranol derivative to a subject in need is disclosed. The tetrahydropyranol derivatives have demonstrated their abilities for reducing tau aggregation.

8 Claims, 7 Drawing Sheets

METHOD FOR TREATING TAU-ASSOCIATED DISEASES USING TETRAHYDROPYRANOL DERIVATIVES

CROSS REFERENCE TO RELATED APPLICATION

This application claims the benefits of the Taiwan Patent Application Serial Number 105125369, filed on Aug. 10, 2016, the subject matter of which is incorporated herein by reference.

BACKGROUND OF THE INVENTION

1. Field of the Invention

The present invention relates to a method for treating tau-associated diseases using tetrahydropyranol derivatives, particularly, to a method for treating Alzheimer's disease (AD) using tetrahydropyranol derivatives.

2. Description of Related Art

Alzheimer's disease (AD) is the most common form of dementia caused by neurodegeneration which may cause progressive cognitive decline and memory loss, and the probability of suffering Alzheimer's disease increases with aging. With the aging populations, the worldwide prevalence of AD will increase to more than 80 million by the year of 2040.

The symptom of AD starts with early memory loss and unstable emotion, then gradually developing to long-term memory loss, abnormal behavior, and evasion of family and the society. Finally, patients will lose their body functions and lead to death. Accordingly, AD not only causes great impact to patient's quality of life but also causes enormous stress to patient's relatives or friends.

The cause and the mechanism of AD remain unclear. The suggested mechanism for the disorder includes cholinergic hypothesis, amyloid hypothesis, and tau hypothesis. The most convincing hypothesis is tau hypothesis, which indicates that the imbalance between the catalytic activities of the kinase and phosphatase results in hyperphosphorylation of tau protein and forming the neurofibrillary tangles that disintegrate the microtubules in the neurons. Accordingly, the delivery system in the neurons is destroyed and results in the death of the neurons.

Therefore, it is desirable to provide effective pharmaceutical compounds to inhibit the aggregation of the tau protein to remiss the progress of AD in order to effectively treat AD.

SUMMARY OF THE INVENTION

In order to solve the aforementioned problems, the present invention provides a method for treating tau-associated diseases, such as Alzheimer's disease caused by tau aggregation, using a tetrahydropyranol derivative.

To achieve the object, the present invention develops a method for treating tau-associated disease comprising: administering a pharmaceutical composition including a tetrahydropyranol derivative to a subject in need, wherein the tetrahydropyranol derivative has the following structure (I):

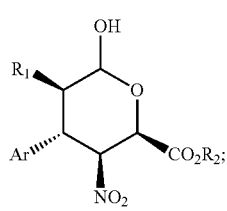

wherein $R_1$, $R_2$ are independently selected from hydrogen and unsubstituted $C_1$-$C_6$ alkyl group; and Ar is an unsubstituted aryl group, or a $C_1$-$C_6$ alkoxy-substituted or an unsubstituted heteroaryl group including N, O, or S atom.

In the present invention, the concentration of the tetrahydropyranol derivative in the pharmaceutical composition is not particularly limited and may be adjusted based on practical usage. For example, the concentration of the tetrahydropyranol derivative in the pharmaceutical composition may be adjusted according to the severity of the disease or other conditions. So that the pharmaceutical composition administered to the subject in need may comprise a therapeutically effective amount of the tetrahydropyranol derivative. In one embodiment of the present invention, the concentration of the tetrahydropyranol derivative may range from 1 nM to 100 μM; and in a preferred embodiment of the present invention, the concentration of the tetrahydropyranol derivative may range from 10 nM to 50 μM.

In one preferred embodiment of the present invention, tetrahydropyranol derivative has the following structure (II):

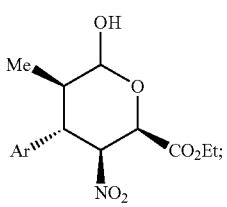

wherein Ar is an unsubstituted aryl group, or a $C_1$-$C_6$ alkoxyl-substituted or an unsubstituted heteroaryl group including N, O, or S atom.

In a most preferred embodiment of the present invention, the tetrahydropyranol derivative has the structures selected from the following compounds (A), (B), and (C):

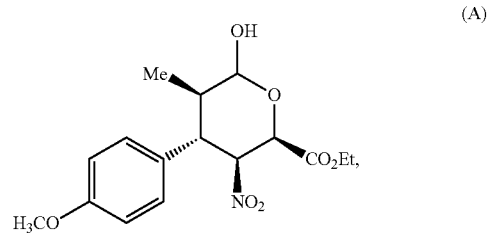

-continued

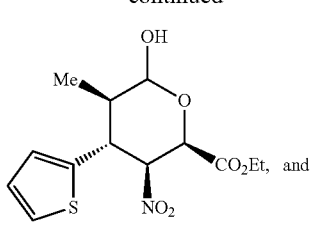
(B)

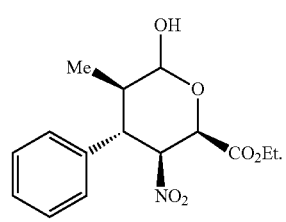
(C)

In the present invention, the tau-associated diseases may comprise those neurodegenerative diseases caused by tau aggregation, especially for those neurodegenerative diseases that caused by tau aggregation in neurons, glial cells, or Lewy bodies. Tau aggregation may cause the formation of the neurofibrillary tangles, which increase the reactive oxygen species (ROS) level and further increase the caspase 3 activity, and eventually leading to neuronal apoptosis. For example, those diseases may be Alzheimer's disease, frontotemporal dementia (Pick's disease), progressive supranuclear palsy, Pugilistic dementia, Lytico-Bodig disease (Parkinson dementia complex), entangled oriented dementia, argyrophilic grain dementia, ganglioglioma, gangliocytoma, subacute sclerosing panencephalitis, lead brain lesions, tuberous sclerosis complex, Hallervorden-Spatz disease, and neuronal ceroid lipofuscinosis; wherein Alzheimer's disease and frontotemporal dementia are the most common tau-associated diseases.

According to the aforementioned description, another subject of the present invention is to provide a method for treating Alzheimer's diseases comprising: administering a pharmaceutical composition including a tetrahydropyranol derivative to a subject in need, wherein the tetrahydropyranol derivative has the following structure (I):

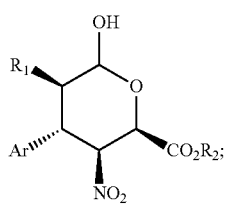
(I)

wherein $R_1$, $R_2$ are independently selected from hydrogen and an unsubstituted $C_1$-$C_6$ alkyl group; and Ar is an unsubstituted aryl group, or $C_1$-$C_6$ alkoxyl-substituted or an unsubstituted heteroaryl group including N, O, or S atom.

In the present invention, the concentration of the tetrahydropyranol derivative in the pharmaceutical composition is not particularly limited and may be adjusted based on practical usage, for example, the concentration of the tetrahydropyranol derivative in the pharmaceutical composition may be adjusted according to the severity of the Alzheimer's disease or other conditions. So that the pharmaceutical composition administered to the subject in need may comprise a therapeutically effective amount of the tetrahydropyranol derivative. In one embodiment of the present invention, the concentration of the tetrahydropyranol derivative may range from 1 nM to 100 μM; and in a preferred embodiment of the present invention, the concentration of the tetrahydropyranol derivative may range from 10 nM to 50 μM.

In one preferred embodiment of the present invention, the tetrahydropyranol derivative has the following structure (II):

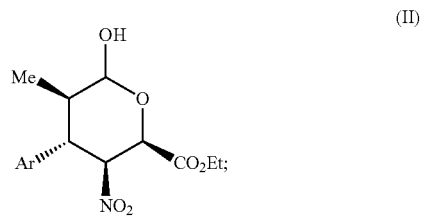
(II)

wherein Ar is an unsubstituted aryl group, or a $C_1$-$C_6$ alkoxyl-substituted or an unsubstituted heteroaryl group including N, O, or S atom.

In the most preferred embodiment of the present invention, the tetrahydropyranol derivative has the structures selected from the following compounds (A), (B), and (C):

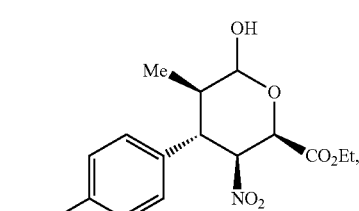
(A)

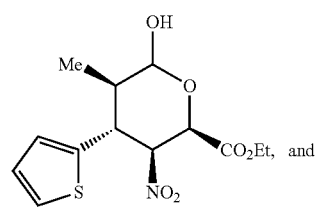
(B)

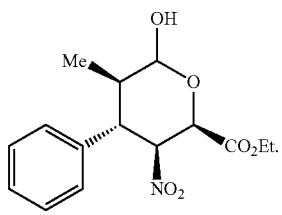
(C)

In order to implement the method according to the present invention, the above pharmaceutical composition including the tetrahydropyranol derivative can be delivered via oral administration, parental administration (such as subcutaneous injection, subdural injection, intravenous injection, intramuscular injection, intrathecal injection, intraperitoneal injection, intracranial injection, intra-arterial injection, or injection at morbid site), topical administration, rectal administration, nasal administration (such as aerosols, inhalants, or powders), sublingual administration, vaginal administration, or implanted reservoir, and so on; but the present invention is not limited thereto.

Hence, the pharmaceutical composition containing the aforementioned tetrahydropyranol derivative can be formulated into health foods or clinical drugs for preventing or treating tau-associated diseases or Alzheimer's disease through any medicine manufacturing procedure. Based on the requirement or usage, the pharmaceutical composition of the present invention may further comprise at least one of a pharmaceutically acceptable carrier, a diluent, or an excipient in the art.

For example, the pharmaceutical composition may be formulated into a solid form or a liquid form. When the pharmaceutical composition is formulated into a solid form, the solid excipient may be powders, pellets, tablets, capsules, and suppositories. The pharmaceutical composition formulated into the solid form may further comprise solid formulations, such as flavoring agents, preservatives, disintegrants, flow aids, and fillers; but the present invention is not limited thereto. In addition, the liquid excipient of the pharmaceutical composition formulated in the liquid form may comprise water, solution, suspension, and emulsifier; and suitable coloring agents, flavoring agents, dispersing agents, antibacterial agents, and stabilizers may also be used to prepare the liquid formulations; but the present invention is not limited thereto.

In the description of the present invention, the term "reduce", "decrease", "ameliorate", or "inhibit" used herein refers to the case that the pharmaceutical composition including the tetrahydropyranol derivative of the present invention is applied to a subject suffering from the disease caused by tau aggregation or suffering from Alzheimer's disease, or having a tendency of developing those aforementioned diseases, in order to achieve the treatment, mitigation, slowing, or improvement of the tendency of the diseases and symptoms.

Herein, the term "therapeutically effective amount" refers to the amount of the tetrahydropyranol derivative for sufficiently inducing the desired medical or pharmaceutical effects. The therapeutically effective amount may be determined by skilled person in the art (such as doctors or pharmacists) by considering various factors such as body type, age, gender, health status, the specific disease involved, the severity of the disease involved, the patient's response, the administration routes, therapy, the co-administered drugs, or other relevant conditions.

In the description of the present invention, the terms "treating" or "treatment" refer to obtaining the desired medical and physiological effects. The medical or physiological effects may refer to preventing or partially preventing a disease, preventing a disease or symptoms of the disease, curing or partially curing a disease, or a therapy for symptoms caused by a disease or adverse effects caused by the disease. The terms "treating" or "treatment" refer to treatment of the mammals, particularly to human diseases. The scope of the treatment comprises preventing a disease, namely prophylactic treatment of a patient who is susceptible to but not yet diagnosed with the disease; inhibiting a disease, that is, inhibiting or reducing the development of a disease or its clinical symptoms; or alleviating a disease, that is, alleviating a disease and/or its clinical symptoms.

In the present invention, "alkyl group" refers to a linear or branched saturated hydrocarbon group. The example of alkyl group includes but not limited to methyl, ethyl, n-propyl, i-propyl, n-butyl, i-butyl, and t-butyl groups.

In the present invention, "alkoxy group" refers to an —O-alkyl group. The example of alkoxy group includes but not limited to methoxy, ethoxy, n-propoxy, i-propoxy, n-butoxy, i-butoxy, sec-butoxy, and t-butoxy groups.

In the present invention, "aryl group" refers to a $C_6$ monocyclic or $C_{10}$ bicyclic aryl group, and each of the rings may be substituted by 1 to 4 substituents. The example of the aryl group includes but not limited to phenyl and naphthyl groups.

In the present invention, "heteroaryl group" refers to a $C_3$-$C_{20}$ cyclic hydrocarbon group with at least one aromatic ring (monocyclic or bicyclic ring), wherein the aromatic ring includes at least one of the heteroatom (such as O, N, or S) and the other atoms of the ring are carbon atom. The example of the heteroaryl group includes but not limited to furyl, pyrrolyl, thienyl, oxazolyl, imidazolyl, thiazolyl, pyridinyl, pyrimidinyl, benzimidazolyl, benzothiazolyl, coumarinyl, quinazolinyl, and indolyl groups.

DETAILED DESCRIPTION OF THE PREFERRED EMBODIMENT

[Statistical Analysis]

For the following values, data are expressed as means±standard deviation (SD). More than three independent experiments were performed for each analysis, and differences between groups were evaluated using a Student's t-test. The p values were two-tailed and were considered statistically significant when p<0.05.

[Preparation of the Compounds]

The preparation methods of the compound (A), (B), and (C) can refer to the description of Ramani Gurubrahamam et al. *Org. Lett.*, 2015, 17 (3), pp 430-433.

[Cell Culture]

We used human embryonic kidney HEK-293 (cultured with DMEM supplemented with 10% FBS) and neuroblastoma SH-SY5Y (cultured with DMEM F12 supplemented with 10% FBS) cells expressing a DsRed-tagged pro-aggregation mutant (ΔK280) of the C-terminal repeat domain of tau ($tau_{RD}$: Gln$^{244}$-Glu$^{372}$ of the longest tau$^{441}$ isoform). The recombinant $tau_{RD}$-DsRed construct was under the control of a hybrid human cytomegalovirus (CMV)/TetO$_2$ promoter that can be induced by adding doxycycline. The Tet-On ΔK280 $tau_{RD}$-DsRed 293 and SH-SY5Y cells were grown in medium containing blasticidin (5 μg/mL) and hygromycin (100 μg/mL) and were used for the following evaluation.

[Embodiment 1]—Evaluation of Cytotoxicity

The HEK-293 cells and SH-SY5Y cells were seeded into a 48-well plate (5×10$^4$), grown for 24 h, and treated with 0.1 μM, 1 μM, 10 μM, 100 μM of compound (A), compound (B), or compound (C) individually for 24 h. Then 20 μL of MTT (5 mg/mL dissolved in PBS) was added for 2 h and the full wavelength microplate spectrophotometer was used for detecting the absorbance of the purple formazan at 570 nm.

Figure 1:
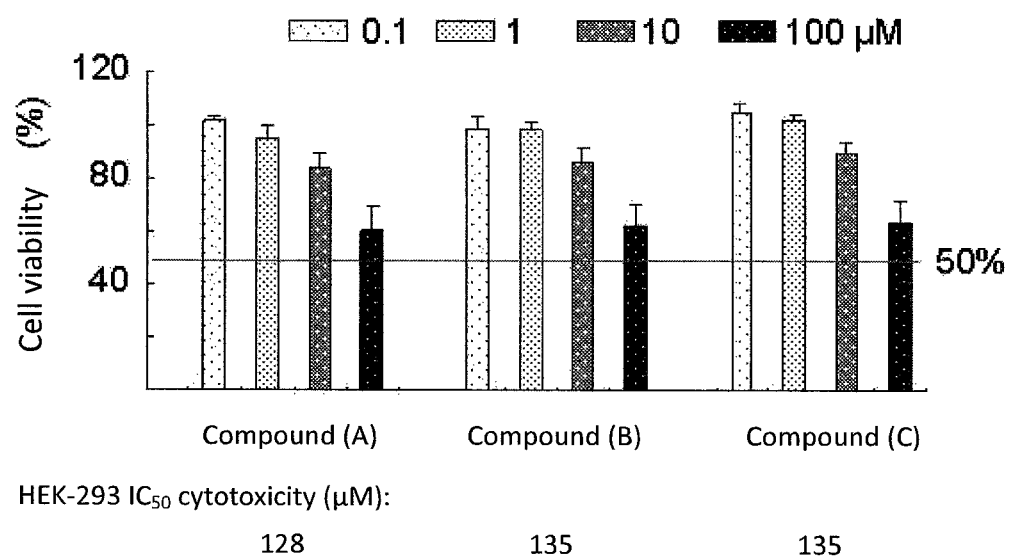
FIG. 1 is an analysis chart showing the cytotoxicity of human HEK-293 cells of a preferred embodiment of the present invention.
Figure 2:
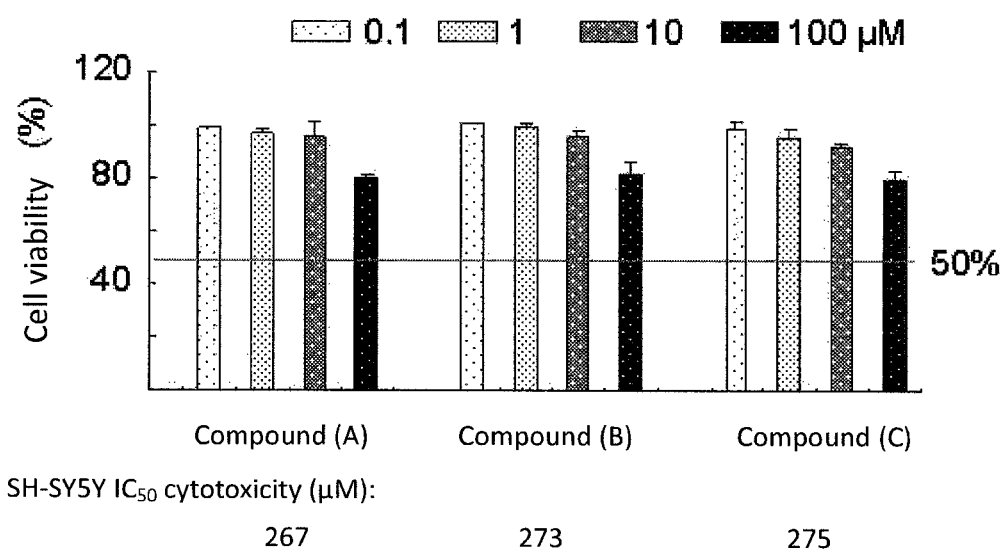
FIG. 2 is an analysis chart showing the cytotoxicity of human SH-SY5Y cells of a preferred embodiment of the present invention.

The results of the cytotoxicity of HEK-293 and SH-SY5Y cells treated with compound (A), compound (B), and compound (C) are shown in FIG. 1 and FIG. 2, wherein the half maximal inhibitory concentration (IC$_{50}$) of compound (A), compound (B), and compound (C) were 128 μM, 135 μM, and 135 μM with respect to HEK-293 cells, and were 267 μM, 273 μM, and 275 μM with respect to SH-SY5Y cells. As a result, the cytotoxicities of compound (A), compound (B), and compound (C) are low and not harmful to the cells.

[Embodiment 2]—Evaluation of Reducing Tau Aggregation

ΔK280 tau$_{RD}$-DsRed 293 cells were seeded into 96-well plates, grown for 24 h, and pretreated with 0.1, 1, 10 μM of congo red (a known tau aggregation inhibitor), compound (A), compound (B), and compound (C) for 8 h. Then doxycycline (Dox; 1 μg/mL) was added for 3 days to induce ΔK280 tau$_{RD}$-DsRed expression and DsRed fluorescence was assessed using a high content analysis (HCA) system.

The DsRed fluorescence of ΔK280 tau$_{RD}$-DsRed fusion protein was used to reflect the aggregation condition of ΔK280 tau$_{RD}$. Misfolding of fused DsRed occurred when ΔK280 tau$_{RD}$ aggregated, and thus decreasing the DsRed fluorescence. Accordingly, inhibition of ΔK280 tau$_{RD}$ aggregation may improve the DsRed misfolding and increase DsRed fluorescence.

Figure 3:
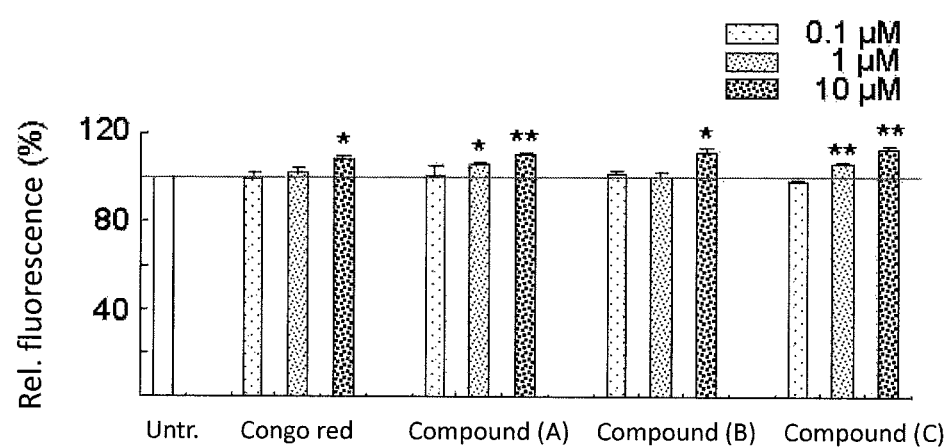
FIG. 3 is an analysis chart showing the inhibition of ΔK280 $tau_{RD}$-DsRed aggregation of a preferred embodiment of the present invention.

The quantification results of the fluorescence microscopy images of untreated cells, cells treated with congo red, compound (A), compound (B), and compound (C) are shown in FIG. 3, wherein the results were analyzed related to 100% fluorescence intensity of the untreated cells. As shown in FIG. 3, the fluorescence intensity of the cells treated with 10 μM of condo red related to that of the untreated cells were 108% vs. 100% (p=0.018); the fluorescence intensities of the cells treated with 1-10 μM of compound (A) related to that of the untreated cells were 105-110% vs. 100% (p=0.016-0.003); the fluorescence intensities of the cells treated with 10 μM of compound (B) related to that of the untreated cells were 111% vs. 100% (p=0.018); and the fluorescence intensities of the cells treated with 1-10 μM of compound (C) related to that of the untreated cells were 106-113% vs. 100% (p=0.004-0.003). Based on the results that described above, compound (A), compound (B), and compound (C) of the present invention have the ability to inhibit ΔK280 tau$_{RD}$ aggregation in HEK-293 cells (*p<0.05, **p<0.01).

Figure 4:
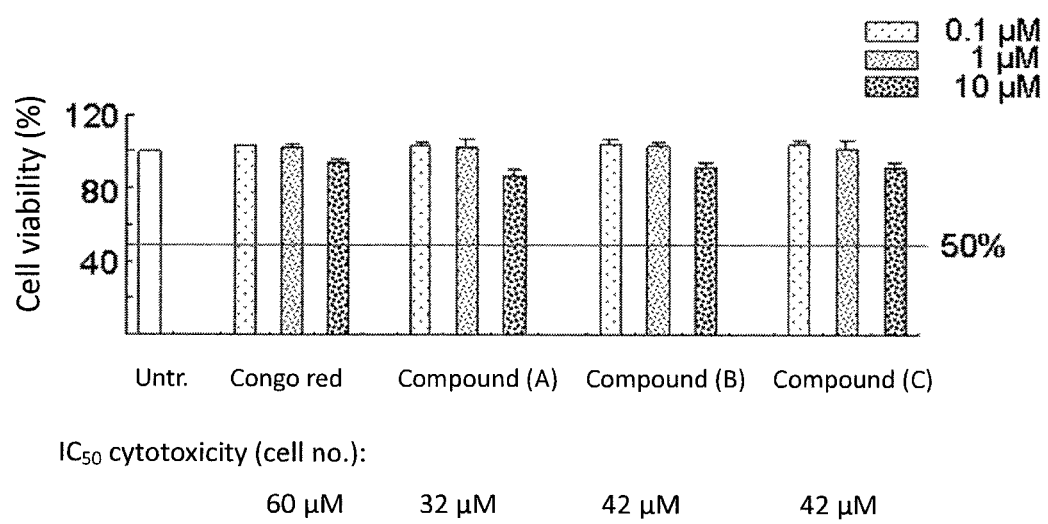
FIG. 4 is an analysis chart showing the cytotoxicity of 293 cells expressing ΔK280 $tau_{RD}$-DsRed fusion protein of a preferred embodiment of the present invention.

Also, as shown in FIG. 4, IC$_{50}$ cytotoxicities of ΔK280 tau$_{RD}$-DsRed 293 cells treated with congo red, compound (A), compound (B), and compound (C) were 60 μM, 32 μM, 42 μM, and 42 μM.

[Embodiment 3]—Evaluation of ROS Level and Caspase 3 Activity

ΔK280 tau$_{RD}$-DsRed 293 cells were seeded into 12-well plates, grown for 24 h, and pretreated with 10 μM of congo red, compound (A), compound (B), and compound (C) respectively for 8 h. Then, doxycycline (1 μg/mL) was added for 3 days to induce ΔK280 tau$_{RD}$-DsRed expression.

Figure 5:
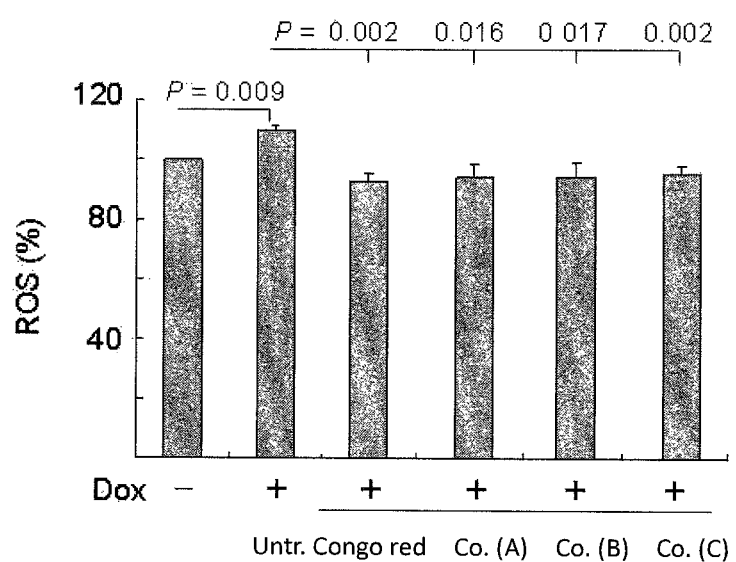
FIG. 5 is a quantification chart showing the ROS level of a preferred embodiment of the present invention.

Next, uninduced cells, doxycycline-induced but compound-untreated cells, and doxycycline-induced and compound-treated cells were incubated with 2',7'-dichlorodihydrofluorecein diacetate (DCFH-DA) in 37° C. for 30 minutes, and then washed with PBS. The excited green fluorescence intensity under 492-495/517-527 nm of excitation/emission wavelength was measured using flow cytometry (BD) to evaluate the ROS level. The evaluation results are shown in FIG. 5.

Figure 6:
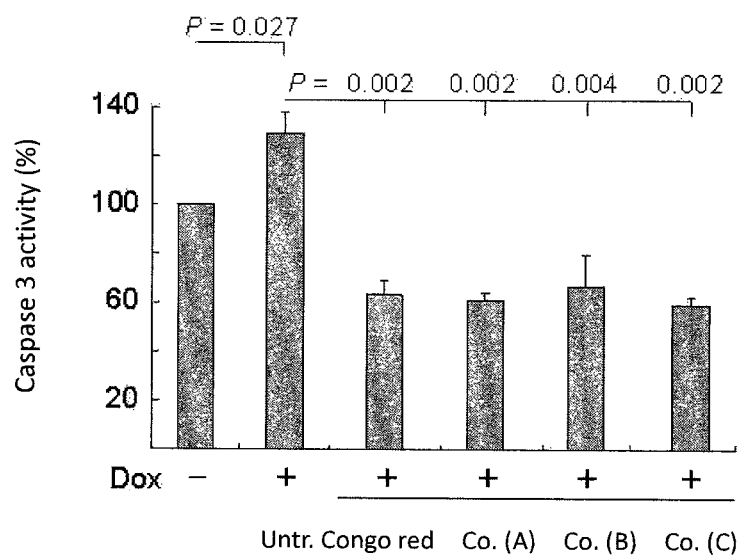
FIG. 6 is quantification chart showing the caspase 3 activity of a preferred embodiment of the present invention.

In addition, the caspase 3 activity of uninduced cells, doxycycline-induced but compound-untreated cells, and doxycycline-induced and compound-treated cells were measured using Caspase 3 Assay Kit (Sigma). 10$^6$ cells in each group were harvested and 100 μL of lysis buffer was added, incubated on the ice for 20 minutes, and then, Ac-DEVD-AMC substrate was added into each group. The release of the fluorescent AMC was recorded under 360/460 nm of excitation/emission wavelength using an FLx800 microplate fluorescence reader (Bio-Tek). The caspase 3 activity was calculated using an AMC standard curve. The evaluation results are shown in FIG. 6.

The cell death caused by ROS usually involves cell necrosis and apoptosis. ROS may be one of the reasons for the cell death caused by neurofibrillary tangles due to tau aggregation, thereby affecting the activity of the downstream caspase 3 and causing cell apoptosis. Based on the analysis results shown in FIG. 5, ROS level of the induced cells significantly increases comparing to the uninduced cells (110% vs. 100%, p=0.009). Comparing to the induced but untreated cells, ROS in the cells treated with congo red significantly decreased (93% vs. 110%, p=0.002), and ROS in cells treated with compound (A), compound (B), or compound (C) also significantly decreased (94-95% vs. 110%, p=0.016-0.002). Further, based on the evaluation results shown in FIG. 6, the caspase 3 activity in the induced cells significantly increased comparing the uninduced cells (129% vs. 100%, p=0.027). Comparing to the induced but untreated cells, caspase 3 activity of the induced cells treated with congo red significantly decreased (63% vs. 129%, p=0.004-0.002), and caspase 3 activity of the induced cells treated with compound (A), compound (B), or compound (C) also significantly decreased (66-59% vs. 129%, p=0.004-0.002).

The evaluation results show that compound (A), compound (B), and compound (C) of the present invention may decrease the ROS level and the activity of caspase 3 in the cells with the tau-associated disease.

[Embodiment 4]—Evaluation of Neuroprotective Effect

ΔK280 tau$_{RD}$-DsRed SH-SY5Y tau$_{RD}$-DsRed cells were seeded in 6-well plate (1×10$^5$/well) in a medium containing all-trans retinoic acid (10 μM), grown for 24 h, and pretreated with 10 μM of congo red, compound (A), compound (B), and compound (C) for 8 h; after which, ΔK280 tau$_{RD}$-DsRed expression was induced with 1 μg/mL doxycycline for 7 days. The cells were then fixed in 4% paraformaldehyde, permeabilized with 0.1% Triton X-100, blocked in 3% BSA, stained with the primary antibody anti-TUBB3 (against neuronal Class III β-tubulin) (1:1000; Convance) and with a secondary anti-rabbit Alexa Fluor® 555 antibody (1:500; Molecular Probes), and then incubated at room temperature for 3 h. Nuclei were counterstained with 4',6-diamidino-2-phenylindole (DAPI). The total outgrowth in the untreated cells, cells treated with congo red, compound (A), compound (B), and compound (C) were assessed using MetaMorph image acquisition and analysis software.

Figure 7:
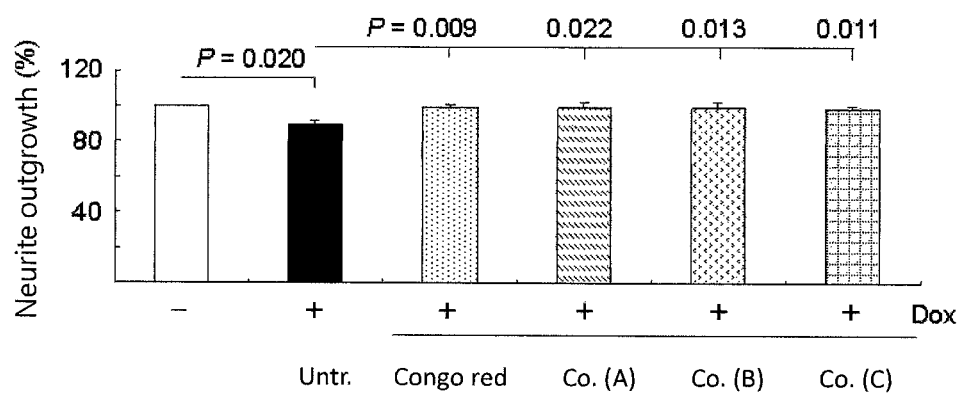
FIG. 7 is a quantification chart showing the neurite growth of a preferred embodiment of the present invention.

According to the fluorescence microscopy images, the quantification of the neurite growth of the uninduced cells, induced but untreated cells, and induced cells treated with congo red, compound (A), compound (B), and compound (C) are shown in FIG. 7. Wherein the quantification of neurite growth of cells induced by doxycycline relative to that of the uninduced cells was 89% vs. 100% (p=0.020) which was significantly decreased; the quantification of neurite growth of induced cells treated with congo red relative to that of the induced but untreated cells was 99% vs. 89% (p=0.009) which was significantly improved; and the quantification of neurite growth of induced cells treated with compound (A), compound (B), and compound (C) relative to that of the induced but untreated cells were 98-99% vs. 89% (p=0.022-0.011) which were also significantly improved.

According to the above evaluations, it is confirmed that the tetrahydropyranol derivatives of the present invention are effective in reducing tau aggregation, reducing ROS level and caspase 3 activity in cell culture model, and has the neuroprotective effect improving neurite growth. The demonstrated effects of the tetrahydropyranol derivatives of the present invention in reducing tau aggregation suggest that they have therapeutic potential in inhibiting or reducing the tau-associated diseases, such as Alzheimer's disease, frontotemporal dementia, or other neurodegenerative diseases, or its clinical symptoms, or have the effect of alleviating these diseases or its clinical symptoms.

What is claimed is:

1. A method for treating neurodegenerative disease caused by tau aggregation, comprising: administering a therapeutically effective amount of a pharmaceutical composition including a tetrahydropyranol derivative to a subject in need, wherein the tetrahydropyranol derivative has the following structure (I):

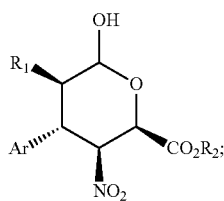

(I)

wherein $R_1$, $R_2$ are independently selected from hydrogen and unsubstituted $C_1$-$C_6$ alkyl group; and Ar is an unsubstituted aryl group, $C_1$-$C_6$ alkoxy-substituted aryl group, or an unsubstituted heteroaryl group including N, O, or S atom.

2. The method as claimed in claim 1, wherein the tetrahydropyranol derivative has the following structure (II):

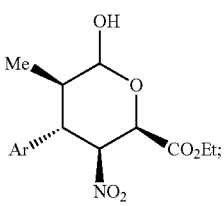

(II)

wherein Ar is an unsubstituted aryl group, or a $C_1$-$C_6$ alkoxy-substituted or an unsubstituted heteroaryl group including N, O, or S atom.

3. The method as claimed in claim 1, wherein the tetrahydropyranol derivative has the structures selected from the following compounds (A), (B), and (C):

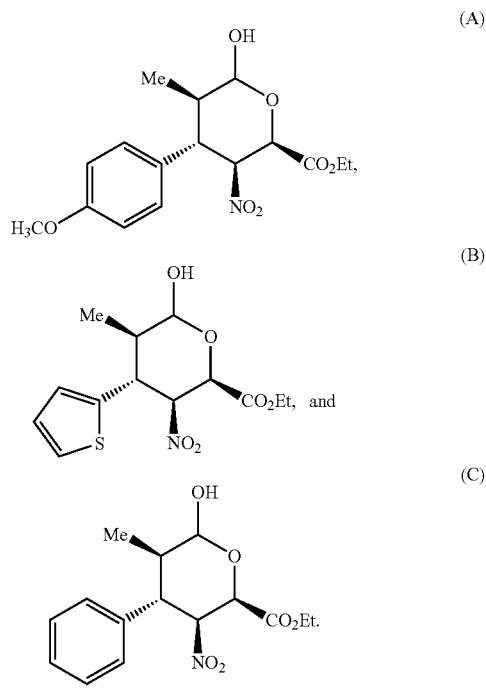

4. The method as claimed in claim 1, wherein the tau-associated disease is a neurodegenerative disease caused by tau aggregation in neurons, glial cells, or Lewy bodies.

5. The method as claimed in claim 1, wherein the tau-associated disease is Alzheimer's disease or frontotemporal dementia.

6. A method for treating Alzheimer's disease, comprising: administering a pharmaceutical composition including a tetrahydropyranol derivative to a subject in need, wherein the tetrahydropyranol derivative has the following structure (I):

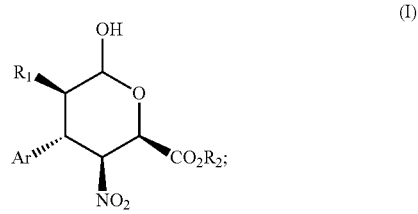

(I)

wherein $R_1$, $R_2$ are independently selected from hydrogen and an unsubstituted $C_1$-$C_6$ alkyl group; and Ar is an unsubstituted aryl group, a $C_1$-$C_6$ alkoxyl-substituted aryl group, or an unsubstituted heteroaryl group including N, O, or S atom.

7. The method as claimed in claim 6, wherein the tetrahydropyranol derivative has the following structure (II):

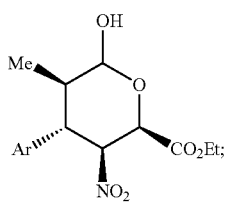
(II)
wherein Ar is an unsubstituted aryl group, or a $C_1$-$C_6$ alkoxyl-substituted or an unsubstituted heteroaryl group including N, O, or S atom.
8. The method as claimed in claim 6, wherein the tetrahydropyranol derivative has the structures selected from the following compounds (A), (B), and (C):
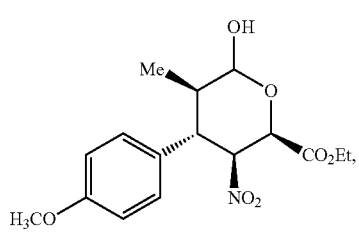
(A)
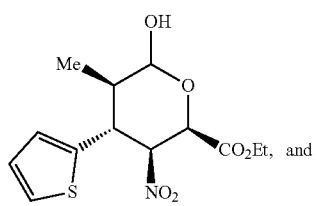
(B)
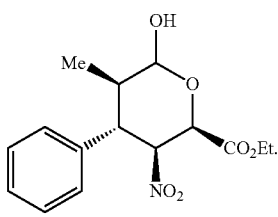
(C)
* * * * *